US007749334B2

(12) United States Patent
Biering et al.

(10) Patent No.: US 7,749,334 B2
(45) Date of Patent: *Jul. 6, 2010

(54) METHODS AND AGENTS FOR CLEANING AND DISINFECTING FRAGILE MEDICAL APPLIANCES

(75) Inventors: Holger Biering, Grevenbroich (DE); Rudolf Glasmacher, Monheim (DE); Hubert Schwidden, Gelsenkirchen (DE); Jorg Sorns, Dusseldorf (DE)

(73) Assignee: Ecolab Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/475,901

(22) Filed: Jun. 1, 2009

(65) Prior Publication Data

US 2009/0238719 A1   Sep. 24, 2009

Related U.S. Application Data

(63) Continuation of application No. 12/202,473, filed on Sep. 2, 2008, now Pat. No. 7,556,698, which is a continuation of application No. 10/945,816, filed on Sep. 20, 2004, now Pat. No. 7,435,303, which is a continuation of application No. 10/168,738, filed as application No. PCT/EP00/12693 on Dec. 14, 2000, now Pat. No. 6,908,891.

(30) Foreign Application Priority Data

Dec. 23, 1999   (DE) .............................. 199 62 344

(51) Int. Cl.
C11D 1/04 (2006.01)
C11D 3/20 (2006.01)
C11D 3/39 (2006.01)
B08B 3/04 (2006.01)

(52) U.S. Cl. .................... 134/36; 510/161; 510/372; 510/393; 510/426; 510/484; 510/488

(58) Field of Classification Search ............. 510/161, 510/372, 393, 426, 484, 488; 134/36
See application file for complete search history.

(56) References Cited

U.S. PATENT DOCUMENTS

| 5,234,719 A | 8/1993 | Richter et al. |
|---|---|---|
| 5,489,434 A | 2/1996 | Oakes et al. |
| 5,567,444 A | 10/1996 | Hei et al. |
| 5,616,335 A | 4/1997 | Nicolle et al. |
| 5,718,910 A | 2/1998 | Oakes et al. |
| 5,720,983 A | 2/1998 | Malone |
| 5,900,256 A | 5/1999 | Scoville, Jr. et al. |
| 6,168,808 B1 | 1/2001 | Godin et al. |
| 6,448,062 B1 | 9/2002 | Huth et al. |
| 6,908,891 B2 * | 6/2005 | Biering et al. ............... 510/161 |
| 6,919,057 B2 | 7/2005 | Halstead et al. |
| 7,056,536 B2 | 6/2006 | Richter et al. |
| 7,435,303 B2 * | 10/2008 | Biering et al. ................ 134/36 |

FOREIGN PATENT DOCUMENTS

| DE | 2655599 | 6/1978 |
|---|---|---|
| DE | 2701133 | 7/1978 |
| DE | 2815400 | 10/1979 |
| DE | 3615787 | 11/1987 |
| DE | 4007758 | 9/1991 |
| DE | 4228786 | 3/1994 |
| DE | 19517465 | 1/1997 |
| EP | 0156275 | 3/1985 |
| EP | 0268227 | 11/1987 |
| EP | 0342499 | 5/1989 |
| EP | 0343605 | 5/1989 |
| EP | 0551975 | 1/1993 |
| EP | 0620013 | 3/1994 |
| EP | 06212170 | 8/1994 |
| EP | 0780374 | 6/1997 |
| EP | 0357238 | 7/1999 |
| EP | 0945140 | 9/1999 |
| FR | 2761080 | 9/1998 |
| WO | WO98/11777 | 3/1998 |

OTHER PUBLICATIONS

Frister et al. "Comparative assessment and optimization of the cleaning performance of automated decontamination processes". Hyg. Med., vol. 19, pp. 673-688 (1994).
Hamo et al. "Testing and evaluating the cleaning and disinfection efficacy of endoscope washer/disinfectors and disinfection automats". Hyg. Med., vol. 20, pp. 41-47 (1995).
Lion et al. "Noveaux decontaminants. Action des peracids a groupe ester sur quelques toxiques insecticides ou de guerre". Bulletin des Societes Chimiques Belges, vol. 100, No. 7, pp. 555-560 (1991) and English abstract.

* cited by examiner

Primary Examiner—Gregory R Del Cotto
(74) Attorney, Agent, or Firm—Merchant & Gould P.C.

(57) ABSTRACT

The invention relates to the use of agents, which contain at least one disinfection system based on selected organic peracids and combinations of peracids, in automatically functioning systems, in which fragile medical appliances, in particular, endoscopes, are cleaned and disinfected. According to the invention, the appliances are brought into contact with an aqueous disinfection agent solution after they have been treated and/or at the same time they are being treated with an aqueous cleaning solution. The invention also relates to cleaning and disinfection agents and methods which are all suited for carrying out this purpose.

10 Claims, No Drawings

METHODS AND AGENTS FOR CLEANING AND DISINFECTING FRAGILE MEDICAL APPLIANCES

CROSS REFERENCE TO RELATED APPLICATION

This application is a continuation of U.S. patent application Ser. No. 12/202,473, filed Sep. 2, 2008, published as 2008-0318826 now U.S. Pat. No. 7,556,698, which is a continuation of U.S. patent application Ser. No. 10/945,816, filed Sep. 20, 2004, now issued as U.S. Pat. No. 7,435,303 which is a continuation of U.S. patent application Ser. No. 10/168,738, filed on Oct. 2, 2002, now issued as U.S. Pat. No. 6,908,891 and claims priority under 35 U.S.C. §365(c) to PCT/EP00/12693, filed on Dec. 14, 2000, the entire disclosures of which are incorporated herein by reference in their entirety.

The present invention relates to the use of compositions containing at least one disinfecting system based on organic per-acids in automatically operating equipment in which sensitive medical apparatus, in particular endoscopes, are cleaned and disinfected, the apparatus being brought into contact with an aqueous disinfectant solution after and/or simultaneously with the treatment with an aqueous cleaning solution. The invention also relates to cleaning compositions and disinfectants and processes suitable for the aforementioned purpose.

Endoscopes, for example flexible glass fiber endoscopes, are used in medical diagnosis and therapy and in surgical operations. In particular, glass fiber endoscopes are extremely complicated precision instruments which possess moving parts and are produced from many materials. The cleaning and disinfection thereof is highly problematic for a number of reasons. Thus, not only the external surfaces of the instrument but also the ducts with narrow lumens in the interior have to be cleaned and disinfected in each case. The apparatus are normally first cleaned and then disinfected by mechanical treatment processes. The thermal disinfection preferred for medical apparatus and instruments cannot be carried out here because endoscopes are produced in part from heat-sensitive materials. With chemothermal treatment, it should be remembered that, although glass fiber endoscopes can be fully immersed in cleaning and disinfecting baths, they withstand at most temperatures to 70° C. without being damaged. It should also be remembered that a number of existing metal parts are susceptible to corrosion, and the elements connecting the individual parts of the apparatus to one another can be attacked by the agents. Furthermore, parts consisting of rubber-like materials may swell and stick. Finally, it should be possible to carry out the cleaning and disinfection of endoscopes in a short period of time so that the instruments are available again as quickly as possible for treating patients.

Mechanical treatment processes are preferred as they allow a standardized procedure which can be checked, if necessary.

A two-stage cleaning process is known from European Patent Application EP-A 0 268 227, whereby the surfaces of the apparatus to be treated, in succession, (a) are brought into contact with a cleaning solution which is heated to 55 to 65° C., is kept at this temperature for 1 to 15 minutes and is subsequently removed and which contains at least one low-sudsing nonionic surfactant, at least one proteolytic enzyme, at least one complexing agent and optionally further conventional cleaning composition constituents and has a pH of 6 to 8 and (b) are brought into contact with a disinfecting solution which is heated to 55 to 65° C., is kept at this temperature for 1 to 15 minutes and is subsequently removed and which contains at least one aldehyde from the group consisting of formaldehyde and aliphatic dialdehydes containing 2 to 8 carbon atoms and at least one complexing agent and has a pH in the range of 6 to 8. The endoscope is subsequently rinsed at least twice with water having a pH between 6 and 8, the water being heated to 55 to 65° C. in the last rinse cycle, and is subsequently dried with sterilized hot air at 55 to 65° C.

European Patent Application EP-A 0 342 499 describes a single-stage process for cleaning and disinfecting endoscopes, wherein the endoscopes are brought into contact with a cleaning disinfectant solution which contains at least one low-suds nonionic surfactant, at least one proteolytic enzyme, at least one complexing agent and at least one aldehyde from the group consisting of formaldehyde and aliphatic dialdehydes containing 2 to 8 carbon atoms and has a pH between 6 and 8, the solution being heated to 55 to 65° C., being kept at this temperature for 1 to 15 minutes and subsequently being removed. The surfaces to be treated are subsequently rinsed twice with water, the water being heated to 55 to 65° C. at least in the last rinsing cycle and are then dried with sterilized hot air at 40 to 60° C.

It is known from European Patent Application EP-A 0 156 275 to use, as antimicrobial substances, amine compounds obtained by reaction of compounds of formula $R^1NHCH_2CH_2CH_2NH_2$, wherein $R^1$ represents a linear alkyl radical containing 12 to 14 carbon atoms, with compounds of formula $R^2OCOCH_2CH_2CHNH_2COOH$, in which $R^2$ represents an alkyl radical containing 1 to 4 carbon atoms or a hydrogen atom, in a molar ratio of 1:1 to 1:2 at 60 to 175° C. These reaction products have also been known as glucoprotamine.

German Patent Application DE-A-40 07 758 describes an aqueous surfactant-containing cleaning composition and disinfectant concentrate which contains, as antimicrobial active ingredients, the amine compounds mentioned in European Patent Application EP-A 0 156 275 in combination with selected quaternary ammonium compounds. A process for the spray cleaning and disinfecting of objects from medical appliances in automatically operated equipment is also described, which comprises the steps a) spraying of an aqueous disinfecting cleaning composition solution at elevated temperature, which has been produced by dilution of the described cleaning composition concentrate and, optionally, b) spraying of an aqueous, optionally surfactant-containing rinsing solution and optionally c) drying, preferably by means of hot air.

EP-A-343 605 describes a liquid aldehyde-free tuberculoidal disinfectant which contains N,N-bis-(3-aminopropyl)-laurylamine as active component.

European Patent Application EP-A 620 013 describes a disinfectant for collective toilet systems and similar arrangements which is inserted manually. It contains salts of amines of formula $RN[(CH_2)_n-NH_2][(CH_2)_m-NH_2]$ or $RNH[(CH_2)_p-NH_2]$, in which R represents a straight-chain or branched alkyl or alkenyl radical containing 6 to 22 carbon atoms, n and m have a value of 4 to 12 and p has a value of 2 to 12. The compositions are used at low temperatures up to 50° C. owing to the corrosiveness in relation to metals such as steel and plastics materials.

European Patent Application EP-A-0 551 975 discloses a disinfectant concentrate and a disinfectant based on amine and alcohol and its use, the alcohol component comprising at least one aromatic alcohol and the amine component at least one secondary and/or tertiary hydroxy group-free alkyl amine. The ready-to-use solution has a pH between 7 and 12. The disinfectant is used, in particular, as a bactericide, in particular as a mycobactericide, fungicide or virucide. European Patent Application EP-A-0 612 170 also relates to an amine- and alcohol-containing disinfectant, wherein the alcohol component comprises at least one glycol ether which is water-miscible to a limited extent and the amine component comprises at least one secondary and/or tertiary hydroxy group-free alkyl amine.

Comparison experiments on fully automated cold chemical and thermochemical endoscope disinfection under practical operating conditions have shown that neither cold chemical nor thermochemical processes allowed completely satisfactory cleaning and disinfection at that time (cf Hyg. Med. 1994, 19, 75 to 93).

The disinfectants and processes described in the foregoing documents have a number of drawbacks. For example, disinfectants based on amine have a tendency to attack metal and plastics materials and to destroy them at temperatures higher than 50° C., so they were expected to be unsuitable for use in mechanical treatment processes for sensitive medical apparatus, for example endoscopes (cf. EP-A-0 620 013). Attempts have also been made to replace the aldehydes used with other compounds, as users complain that there is a risk of exceeding MAC values and that personnel involved with the cleaning apparatus may be injured by the aldehydes. Furthermore, aldehydes lead to the fixing of protein-containing soil if the soil has not been removed completely by a preliminary cleaning stage.

It is known that quaternary ammonium compounds have a good disinfecting action but are attracted to surfaces and may cause adhesion.

It is known that peroxides have a broad range of antimicrobial activity.

For example, it has been proposed in German Offenlegungsschriften 26 55 599 and 28 15 400 that the aqueous preparations required for disinfection are produced just prior to use, from relatively stable preliminary stages, namely from sodium perborate and acid anhydrides. According to German Offenlegungsschrift 27 01 133, the aqueous preparations are obtained from hydrogen peroxide eliminators and aromatic acyloxycarboxylic acids. However, only a few of these compounds yield disinfecting solutions with sufficiently broad activity, and these acylation agents mixed with the necessary inorganic peroxides can only be stored for a limited period owing to decomposition reactions. There is a commercially available product known as Sekusept powder which, when dissolved in water, produces a disinfecting preparation by reaction of sodium perborate with tetraacetyl ethylenediamine (TAED). This product which is based on an N-acyl compound has a broad range of activity and is stable in storage. Although this has enabled a high standard to be achieved in the disinfection of medical instruments, further attempts have been made to improve peroxidic systems in order to overcome remaining deficiencies and drawbacks in use. It has been proposed, for example in DE-OS 36 15 787, that the magnesium salt of monoperoxy phthalic acid be used instead of inorganic hydrogen peroxide eliminators in the production of these preparations. However, the use of this organic peroxide involves much higher production costs than the use of inexpensive inorganic peroxides which are stable in storage.

EP 357 238 relates to antimicrobial compositions which contain copper and brass corrosion inhibitors, a buffer substance, an anticorrosion agent which inhibits the corrosion of various metals and a wetting agent in addition to a strong oxidizing agent selected from peracetic acid and lithium hypochlorite. In the description, the patent deals in more detail with the use of these agents for the disinfection by immersion of, for example, sensitive medical apparatus such as endoscopes and the like. The complex composition of the peracetic acid formulations protected in this document is probably due to the fact that the risk of corrosion during disinfection by immersion is high owing to the generally very long contact times.

This complexity of the per-acid formulations can be avoided by carrying out processes which allow thorough cleaning and disinfection to be achieved within a comparatively short period of time. For example, EP 945 140 describes a machine and a process for the washing and disinfection/sterilization of endoscopes in which dosing agents for the dosing of oxide-based disinfecting/sterilizing solutions are used. Disinfection is therefore achieved within a short period of time. Additions of corrosion inhibitors are unnecessary. Furthermore, the automatic cleaning, washing and disinfecting process is assisted by an additional mechanical effect. This is achieved in that the washing and disinfecting solution is kept in motion, at least in part, in the automatically controlled process and an additional mechanical effect is created by the rinsing and/or spraying operations.

However, the use of peracetic acid in the immersion process or use of oxide-based disinfecting/sterilizing solutions in the automatic cleaning and disinfecting of endoscopes known from the state of the art is also accompanied by drawbacks. Peracetic acid itself has an unpleasant odor and is particularly problematic if it is to be used by personnel with inadequate chemical training. Furthermore, peracetic acid has deficiencies over the entire range of germs, in particular in the case of fungi and yeasts. Other oxide-based disinfecting solutions are either accompanied by similar drawbacks with respect to the odor or similarly have inadequate antimicrobial activity which is required, in particular, in relation to *Mycobacterium terrae*. In addition, the per-acids normally used for disinfection purposes do not have a cleaning activity if residual soil has not been completely removed by a preliminary cleaning stage.

It was accordingly the object of the present invention to seek compositions for use in automatically operating equipment in which sensitive apparatus, in particular endoscopes, are cleaned and disinfected, which compositions may be used in a low concentration and with minimal odor owing to their excellent effectiveness. A further object of the present invention is to achieve an additional cleaning effect with the disinfecting solution based on organic per-acids so that it is additionally assured that the medical apparatus are free from residues if cleaning in the first stage of the automatic cleaning and disinfecting process is incomplete.

The present invention accordingly relates to the use of compositions containing at least one disinfecting system based on organic per-acids comprising, as per-acids or salts of per-acids, a) compounds of general formula I

$$R^2-O_2C-(CH_2)_x-CO_3H \quad \quad (I)$$

wherein $R^2$ is hydrogen or an alkyl group containing 1 to 4 carbon atoms and x is a number from 1 to 4 and/or b) compounds from the group consisting of phthalimido percarboxylic acids (II), wherein the percarboxylic acid content is 1 to 18 carbon atoms optionally in combination with other per-acids or containing as per-acids or salts of per-acids, c) compounds of general formula I

$$R-O_2C-(CH_2)_x-CO_3H \quad \quad (I)$$

wherein R is hydrogen or an alkyl group containing 1 to 4 carbon atoms and x is a number from 1 to 4 and/or compounds from the group consisting of phthalimido percarboxylic acids (II), wherein the percarboxylic acid content is 1 to 18 carbon atoms, and/or
compounds of general formula III

 R—CO$_3$H  (III)

wherein R represents an alkyl or alkenyl group containing 1 to 18 carbon atoms, in combination with
c1) at least one fatty acid and/or
c2) at least one hydrotrope and/or
c3) at least one surfactant component and/or
c4) at least one complexing component in aqueous disinfectant solutions for automatically operating equipment in which sensitive medical apparatus, in particular endoscopes, are cleaned and disinfected, wherein the apparatus are brought into contact with this aqueous disinfectant solution after and/or simultaneously with the treatment with an aqueous cleaning solution.

It is preferred if the ingredients combine to form a synergistic combination in the aqueous disinfecting solution.

It is also preferred if the contact time between the aqueous disinfectant solutions and the sensitive medical apparatus is between 1 and 15 minutes.

The use according to the invention is preferably at a temperature between 5 and 55° C., particularly preferably between 15 and 45° C.

It is also preferable if the pH is between 5 and 9, particularly preferably 6.5 to 8, during the use according to the invention.

In a preferred practical example of the present invention, for producing the aqueous disinfectant solution,
a) hydrogen peroxide or peroxidic compounds which form hydrogen peroxide in water are reacted in an aqueous acidic medium with carboxylic acids or carboxylic acid derivatives which are known as starting products for per-acid compounds of formulae I, II, III, and optionally further components and subsequently
b) the pH of the preparation obtained in step a) or of the dilute preparation is adjusted to a pH between 5 and 9, particularly preferably between 6.5 and 8, the use of a buffer solution intended for pH adjustment being most particularly preferred.

It is also preferred if, for producing the aqueous disinfectant solution,
a) hydrogen peroxide or peroxidic compounds which form hydrogen peroxide in water are reacted in an aqueous alkaline medium with N-carboxylic acid amides which are known as starting products for per-acid compounds of formulae I, II, III and optionally further components and subsequently
b) the pH of the preparation obtained in step a) or of the dilute preparation is adjusted to a pH of between 5 and 9, particularly preferably between 6.5 and 8, the use of a buffer solution intended for pH adjustment being most particularly preferred.

N-acylcaprolactam and TAED are mentioned as N-carboxylic acid amides.

It is preferable if the apparatus are rinsed with water and subsequently dried in a manner known per se after separation of the aqueous disinfectant solution.

Preferably, the compositions to be used according to the invention are optionally brought into contact with the medical apparatus to be treated by spraying, rinsing, immersion and/or other procedures after an intermediate dilution or mixing stage.

Preferred practical examples of the compositions to be used according to the invention contain a) per-acids in which R$^2$ is hydrogen or a methyl group as per-acids of general formula I, and/or
b) phthalimido-percarboxylic acids in which the percarboxylic acid content comprises 1 to 8 carbon atoms as per-acids, and/or
c) per-acids with an alkyl or alkenyl group comprising 1 to 12 carbon atoms as per-acids of general formula III.

It is particularly preferred if one or more compounds selected from peracetic acid, perpropionic acid, peroctanoic acid, phthalimidoperhexanoic acid, phthalimidoperoctanoic acid, perglycolic acid, perglycolic acid monomethyl ester, persuccinic acid, persuccinic acid monomethyl ester, perglutaric acid, perglutaric acid monomethyl ester, peradipic acid, peradipic acid monomethyl ester are contained as per-acids.

The preferred content of per-acids in the solutions which come into contact with the medical apparatus according to the present invention is 0.001 to 0.5% by weight, particularly preferably 0.01 to 0.2% by weight, based on the total disinfecting solution.

It is also preferred if an additional content of 0.0001 to 2.5% by weight, particularly preferably 0.001 to 0.5% by weight, of hydrogen peroxide comes into contact with the medical apparatus during the use according to the invention.

Moreover, it is preferred with the use according to the invention that the non-oxidized acid corresponding to the per-acid present and, in the case of per-acid esters, the non-esterified form of the non-oxidized acid also comes into contact with the medical apparatus.

The compositions to be used according to the invention contain fatty acids containing 8 to 12 carbon atoms, particularly preferably octanoic acid, as preferred fatty acids c1).

If the compositions to be used according to the invention contain complexing components c4), these are preferably selected from components having complexing properties for polyvalent metal ions.

Examples of components with complexing properties include nitrilotriacetic acid, ethylenediamine tetraacetic acid, methylglycine diacetic acid, gluconic acid, citric acid, dicarboxymethyl-L-glutamic acid, serine diacetic acid, imidosuccinic acid, the polycarboxylic and phosphonic acid group and the respective salts thereof. Examples of polycarboxylic acids include polyacrylic acids and copolymers of maleic acid anhydride and acrylic acid as well as the sodium salts of these polymeric acids. Conventional commercial products include Sokalan® CP 5 and PA 30 made by BASF, Alcosperse® 175 and 177 made by Alco, LMW® 45 N and SPO2 ND made by Norsohaas. Suitable natural polymers include oxidised starch (for example, DE 42 28 786) and polyamino acids such as polyglutamic acid or polyaspartic acid made by Cygnus, Bayer, Rohm & Haas, Rhône-Poulenc or SRCHEM, for example.

Examples of phosphonic acids include 1-hydroxyethane-1,1-diphosphonic acid, diethylenetriamine pentamethylene phosphonic acid or ethylenediamine tetramethylene phosphonic acid and the alkali salts thereof.

If the compositions to be used according to the invention contain surfactant components c3), these are preferably selected from the groups consisting of anionic, cationic, nonionic, amphoteric surfactants, alkylamine oxides, siloxane-based surfactants and surfactant phosphoric acid esters and salts thereof.

Preferred surfactant components include anionic surfactants conventionally used in the field of detergents and cleaning compositions, for example $C_8$-$C_{18}$ alkylsulfates, $C_8$-$C_{18}$ alkylethersulfates, $C_8$-$C_{18}$ alkanesulfonates, $C_8$-$C_{18}$ olefin sulfonates, sulfonated $C_8$-$C_{18}$ fatty acids, $C_8$-$C_{18}$ alkylbenzenesulfonates, sulfosuccinic acid mono- and di-$C_1$-$C_{12}$ alkyl esters, $C_8$-$C_{18}$ alkylpolyglycolethercarboxylates, $C_8$-$C_{18}$ N-acyltaurides, $C_8$-$C_{18}$ N-sarcosinates, $C_8$-$C_{18}$ alkylisothionates and mixtures thereof.

Trialkylamine oxide with an alkyl group containing 8 to 20 carbon atoms and two alkyl groups with a smaller number of carbon atoms in the alkyl chain is preferably contained as amine oxide, wherein the two shorter alkyl groups may be the same or different and the amine oxide derivative is particularly preferably tallow grease-bis-(2-hydroxyethyl)-amine oxide, oleyl-bis-(2-hydroxyethyl)-amine oxide, coconut-bis-(2-hydroxyethyl)-amine oxide, tetradecyldimethyl-amine oxide and/or alkyldimethyl-amine oxide containing 12 to 18 carbon atoms in the alkyl chain.

The nonionic surfactants in the compositions to be used according to the invention are preferably alkylpolyglycosides which can normally be obtained industrially by condensation of fatty alcohols with glucose or polyglucose and are commercially available in various forms. Examples of alkylpolyglycosides which are particularly suitable for the use according to the invention include the products Glucopon® 600 made by Henkel and Triton® BG10 made by Rohm & Haas.

Further preferred nonionic surfactants include alkoxylated alkyl alcohols containing 8 to 22 carbon atoms in the alkyl chain wherein, in particular, at least one compound from the groups consisting of mixed ethoxylates/propoxylates of branched or unbranched alkyl alcohols containing 8 to 22 carbon atoms in the alkyl chain and ethoxylates comprising terminal groups, of branched or unbranched alkyl alcohols containing 8 to 22 carbon atoms in the alkyl chain is contained, and quite particularly preferably at least one compound from the groups consisting of ethoxylated and propoxylated alkyl alcohols containing 12 to 22 carbon atoms in the alkyl part, the butyl ethers of ethoxylated alkyl alcohols containing 12 to 22 carbon atoms in the alkyl part and methyl ethers of ethoxylated alkyl alcohols containing 12 to 22 carbon atoms in the alkyl part, butyl ether and methyl ether of the ethoxylated 2-octyl-1-dodecanol being contained in the specific case. Nonionic surfactants which are particularly suitable for producing the formulations according to the invention include, for example, Plurafac® LF 403, Plurafac® 431 made by BASF and Dehypon® LT 104 and Dehypon® G 2084 made by Henkel.

Phosphoric acid ester compounds, preferably including at least one salt of a phosphoric acid partial ester, are preferably used as surfactant in the composition to be used according to the invention, at least one alkali salt of a phosphoric acid partial ester of alkoxylated alkyl phenol particularly preferably being used.

Phosphoric acid esters are surfactant substances preferably derived from long-chain aliphatic or araliphatic alcohols. Salts of phosphoric acid partial esters have proven particularly suitable, in particular the salts of alkoxylated alkyl phenols in this case. Sodium and potassium salts are preferably used as alkali salts, the potassium salts being particularly preferred. Surfactant phosphoric acid partial esters of the type which are preferably used according to the invention are commercially available. An example of an active ingredient of this type which is particularly suitable according to the invention is the product Triton® H 66 (Rohm & Haas).

It is also preferable to select the hydrotrope c3) from the groups consisting of anionic surfactants which have already been dealt with in the foregoing text but will be mentioned again owing to the specific function. Particularly preferred hydrotropes include sulfonates/sulfonic acids, in particular cumene, xylene, octyl, naphthyl and alkylbenzenesulfonates/sulfonic acids, the alkyl group containing between 6 and 16 carbon atoms in the last case.

It is also preferred if cleaning and disinfection take place in succession in time in an automatic treatment process.

In a further preferred practical example, cleaning and disinfection take place simultaneously in time in an automatic treatment process.

The present invention also relates to cleaning compositions and disinfectants for sensitive medical apparatus, in particular endoscopes, which are based on organic per-acids or salts of organic per-acids selected from a) compounds of general formula I

$$R-O_2C-(CH_2)_x-CO_3H \qquad (I)$$

wherein R is hydrogen or an alkyl group containing 1 to 4 carbon atoms and x is a number from 1 to 4 and/or b) compounds from the group consisting of phthalimido percarboxylic acids (II), wherein the percarboxylic acid content is 1 to 18 carbon atoms and/or c) compounds of general formula I

$$R-O_2C-(CH_2)_x-CO_3H \qquad (I)$$

wherein R is hydrogen or an alkyl group containing 1 to 4 carbon atoms and x is a number from 1 to 4 and/or compounds from the group consisting of phthalimido percarboxylic acids (II), wherein the percarboxylic acid content comprises 1 to 18 carbon atoms, and/or compounds of general formula III

$$R-CO_3H \qquad (III)$$

wherein R represents an alkyl or alkenyl group containing 1 to 18 carbon atoms, in combination with c1) at least one fatty acid and/or c2) at least one hydrotrope and/or c3) at least one surfactant component and/or c4) at least one complexing component.

The foregoing explanations concerning the make-up of the compositions to be used according to the invention are also preferred practical examples of the disinfectant according to the invention for sensitive medical apparatus.

The present invention also relates to a process for cleaning and disinfecting sensitive medical apparatus, in particular endoscopes, in automatically operating equipment, in which the apparatus are treated with a neutral or alkaline cleaning solution optionally containing enzymes in a first step and, optionally after intermediate rinsing with water, the apparatus are brought into contact with an aqueous solution of a cleaning composition and disinfectant according to the invention in a second step, and the apparatus are rinsed with water and then optionally dried in a third step.

Here also, the foregoing explanations concerning the make-up of the compositions to be used according to the invention are also preferred practical examples of the cleaning composition and disinfectant for sensitive medical apparatus.

EXAMPLES

Example 1

Concentrates having the following composition have been produced by mechanical combination of the individual constituents:

| Cleaning composition concentrate | |
| --- | --- |
| 10% by weight | n-butyl ether of an addition product of 9.5 mol ethylene oxide to 1 mol hardened tallow grease alcohol (Dehypon LT 104, commercial product made by Henkel KgaA) |
| 3% by weight | 1,2-propylene glycol |
| 3% by weight | sodium cumene sulfonate |
| 7% by weight | triethanolamine |
| 1% by weight | citric acid |
| to 100% by weight | water |

| Disinfectant concentrate | |
| --- | --- |
| 5% by weight | peracetic acid |
| 25% by weight | hydrogen peroxide |
| 6% by weight | acetic acid |
| 1% by weight | 1-hydroxyethane-1,1-diphosphonic acid |
| to 100% by weight | water |

| Buffer solution | |
| --- | --- |
| 5% by weight | sodium hydroxide |
| 1% by weight | potassium tripolyphosphate |
| to 100% by weight | water |

The endoscopes were cleaned and disinfected in a sealable stainless steel vessel (about 60 cm×60 cm×65 cm) which was provided with a heater and had been equipped with feed and discharge pipes for the cleaning composition and disinfectant solution and the water used in the rinsing cycles and for the hot air required for drying the apparatus.

Using a circulation pump, the liquids present in each case could be pumped into contact with the external surfaces of the apparatus by means of a so-called spray arm and through the ducts of the endoscope by means of special connections.

The experiments were carried out using conventional commercial endoscopes.

Water adjusted to a hardness of 5° d using a cation exchanger was used to apply the cleaning composition and disinfectant solutions.

Ready-to-use cleaning composition and disinfectant solutions were produced by diluting appropriate amounts of cleaning concentrate, disinfectant concentrate and buffer solution.

The cleaning solution was adjusted to contain 0.5 g surfactant/l in the solution for application.

The disinfectant solution was prepared so that it contained 0.5 g peracetic acid/l in the solution for application.

The endoscopes in a wire basket were immersed into the stainless steel container when carrying out the cleaning and disinfecting process. The ducts of the endoscopes were attached to the circulation pump. Sufficient liquid was supplied to the stainless steel container in each of the individual stages of the process for the external surface of the endoscopes to be sprayed intensively in a circulatory process and at the same time for the liquid to be pumped continuously through the ducts of the endoscope.

The cleaning concentrate was dosed in a strength of 0.5% at 20° C., the cleaning solution circulated via the spray arm and through the ducts and heated to 35° C. Once the temperature was reached, the cleaning process was continued for a further 2 minutes under constant conditions.

Two procedures designated hereinafter as test 1 and test 2 were investigated for the subsequent disinfecting stage:

Test 1:

The cleaning solution was pumped away and disposed of and the endoscope then filled with fresh water which had been mixed with 1% by weight of the disinfectant concentrate and with 1% by weight of the buffer solution, based on the total aqueous solution.

Test 2:

1% by weight of the disinfectant concentrate and 1% by weight of the buffer solution, based on the total cleaning solution present, were dosed into the cleaning solution.

The solutions presented in test 1 and in test 2 were heated to 35° C. and circulated via the spray arm and through the ducts for a period of 5 minutes and therefore brought into contact with the internal and external surfaces of the endoscope to be treated.

The solutions were pumped away and the endoscope rinsed twice internally and externally with cold water.

To test the cleaning effect achieved with the process according to the invention, the instrumentation duct of the endoscope was provided with artificial soil having the following composition:

9.85% by weight of heparinized sheep's blood
0.15% by weight of protamine 1000

To determine the cleaning capacity, the endoscope was inspected for residues. For this purpose, the ducts were rinsed with a 1% aqueous sodium dodecylsulfonate solution and the protein content determined by the OPA method (cf. H. Frister and W. Michels, Hyg. Med. 1994, 19, 673 to 688).

To check the disinfecting activity achieved with the process according to the invention, 'Test 1 and Test 2', the ducts of the endoscope were contaminated with a blood/germ suspension containing the following germs:

a) about $10^9$ germs/ml of Staphylococcus aureus b) about $10^9$ germs/ml Pseudomonas aeroginosa c) about $10^9$ germs/ml Enterococcus faecium 0.35% by weight of the germ suspension were mixed with 9.5% by weight of heparinized sheep's blood and 0.15% by weight of protamine 1000 in each case. This blood/germ suspension was then used to soil the instrumentation duct (cf Hyg. Med. 1995, 20, 4047).

After carrying out the process according to the invention, 'Test 1 and Test 2', 0.5 l of a solution containing 3% by weight Tween 80, 0.3% by weight lecithin, 0.1% histidine, 0.1% by weight trypton and 0.05% by weight sodium chloride was aspirated through the ducts of the endoscope. Samples each consisting of 1 ml of this solution were inoculated onto agar plates which were subsequently fertilized for at least 48 hours at 37° C. and 72 hours at 35° C. and then inspected for the existence of germ propagation. It has been found that, when carrying out the process according to the invention in both variant 'Test 1' and variant 'Test 2', residual soiling could not be detected and the necessary freedom from germs had been achieved.

Further tests carried out under the above-described conditions demonstrated that the processes according to the invention according to 'Test 1 and Test 2' could also be successfully used in the case of contamination by viruses, in particular entero viruses such as polio viruses, and also heat-resistant viruses such as papovaviruses.

Example 2

The antimicrobial range of activity of various combinations of per-acids with selected additives was investigated at ambient temperature by the DVG (Deutsche Vererinärgesellschaft e.V.) quantitative suspension test in a second series of tests.

*Staphylococcus aureus* and *Escherichia coli* were used as test germs for determining the bactericidal activity. *Saccharomyces cerevisiae* and *Aspergillus niger* were used as test germs for determining the fungicidal activity. Table 2 shows the formulations tested. Table 3 and Table 4 show the results of the quantitative suspension test.

It can been seen from the tabulated results that the range of activity of per-acids can be significantly improved by selected combinations. This is particularly important because safety during the automatic cleaning and disinfecting of sensitive medical apparatus can thus be improved.

The additional components such as sulfonates/sulfonic acids, surfactants and fatty acids are also known to have additional cleaning effects, so it is possible to remove, in a subsequent disinfecting stage, any residual soil which could not be removed in a first cleaning stage.

TABLE 2

Formulations for the microbiological experiment

| Raw material | Form. 1 | Form. 2 | Form. 3 | Form. 4 | Form. 5 | Comparison form. 1 | Comparison form. 2 |
|---|---|---|---|---|---|---|---|
| Perglutaric acid monomethyl ester (10%) | 80 | 80 | 80 | 80 | — | — | 100 |
| Peracetic acid (10%) | — | — | — | — | 80 | 100 | — |
| Alkylbenzene-sulfonic acid | 10 | — | — | 10 | 10 | — | — |
| Dimethylcoconut-amine oxide | — | 10 | — | — | — | — | — |
| Sodium octyl sulfonate | — | — | 16 | 6 | 6 | — | — |
| Octanoic acid | — | — | 4 | 4 | 4 | — | — |
| Water | 10 | 10 | — | — | — | — | — |

TABLE 3

Results of the microbiological experiments against bacteria

| Product | [AWK] % | *Staphylococcus aureus* ATCC 6538 (K 3212) Inoculum $7.05 \times 10^8$ KBE/ml | | *Escherichia coli* ATCC 10536 (K 2124) Inoculum $1.07 \times 10^9$ KBE/ml | |
|---|---|---|---|---|---|
| | | 1 minute RF | 5 minutes RF | 1 minute RF | 5 minutes RF |
| Comparison formulation 1 | 0.1 | 1.3 | >4.87 | >5.2 | >5.3 |
| | 0.3 | 3.4 | >4.87 | >5.2 | >5.3 |
| Comparison formulation 2 | 0.1 | 0.04 | >4.87 | 3.69 | >5.3 |
| | 0.3 | 0.59 | >4.87 | >5.2 | >5.3 |
| Formulation 1 | 0.1 | 3.42 | >4.87 | >5.2 | >5.3 |
| | 0.3 | >4.9 | >4.87 | >5.2 | >5.3 |
| Formulation 2 | 0.1 | 0 | 0.09 | 1.17 | >5.3 |
| | 0.3 | 0.03 | >4.87 | >5.2 | >5.3 |
| Formulation 3 | 0.1 | >4.9 | >4.87 | >5.2 | >5.3 |
| | 0.3 | >4.9 | >4.87 | >5.2 | >5.3 |
| Formulation 4 | 0.1 | 3.04 | >4.87 | >5.2 | >5.3 |
| | 0.3 | >4.9 | >4.87 | >5.2 | >5.3 |
| Formulation 5 | 0.1 | 3.2 | >4.87 | >5.2 | >5.3 |
| | 0.3 | >4.9 | >4.87 | >5.2 | >5.3 |

AWK = concentration for application; RF values = germ reduction in LOG stages

TABLE 4

Table of results for DVG fungicidal activity

| Product | [AWK] % | *Saccharomyces cerevisiae* ATCC 9763 (K 5011) Inoculum $1.36 \times 10^7$ KBE/ml | | *Aspergillus niger* ATCC 16404 (K 7444) Inoculum $1.07 \times 10^9$ KBE/ml | |
|---|---|---|---|---|---|
| | | 5 minutes RF | 30 minutes RF | 5 minutes RF | 30 minutes RF |
| Comparison formulation 1 | 0.3 | 0.53 | 0.55 | 0 | 0 |
| | 1.0 | 0.71 | 1.4 | 0 | 0 |
| Comparison formulation 2 | 0.3 | 0.21 | 0.24 | 0 | 0 |
| | 1.0 | 0.24 | 1.1 | 0 | 0 |

TABLE 4-continued

Table of results for DVG fungicidal activity

| Product | [AWK] % | Saccharomyces cerevisiae ATCC 9763 (K 5011) Inoculum 1.36 × 10$^7$ KBE/ml | | Aspergillus niger ATCC 16404 (K 7444) Inoculum 1.07 × 10$^9$ KBE/ml | |
|---|---|---|---|---|---|
| | | 5 minutes RF | 30 minutes RF | 5 minutes RF | 30 minutes RF |
| Formulation 1 | 0.3 | 2.88 | >3.19 | 0 | 0 |
| | 1.0 | >3.18 | >3.19 | 0 | 0.02 |
| Formulation 2 | 0.3 | 0.55 | >3.19 | 0 | 0.38 |
| | 1.0 | >3.18 | >3.19 | 0.22 | 0.85 |
| Formulation 3 | 0.3 | >3.18 | >3.19 | 0.31 | 0.54 |
| | 1.0 | >3.18 | >3.19 | 1.56 | 4.02 |
| Formulation 4 | 0.3 | 3.18 | 3.19 | 0.39 | 0.87 |
| | 1.0 | 3.18 | 3.19 | 1.34 | >4.02 |
| Formulation 5 | 0.3 | 3.18 | 3.19 | 0.61 | 1.3 |
| | 1.0 | 3.18 | 3.19 | 1.74 | >4.02 |

AWK = concentration for application; RF values = germ reduction in LOG stages

What is claimed is:

1. A method for cleaning and disinfecting an endoscope comprising:
    contacting the endoscope with a neutral or alkaline cleaning composition;
    contacting the endoscope with an aqueous antimicrobial composition comprising peroctanoic acid, and a fatty acid containing 8 to 12 carbon atoms and having a pH from 6.5 to 8; and
    rinsing the endoscope with water; wherein the cleaning composition does not comprise an oxidizing agent, the step of contacting the endoscope with the cleaning and antimicrobial compositions are carried out simultaneously with respect to time, and further wherein the cleaning composition and the antimicrobial composition are applied to the endoscope separately.

2. The method of claim 1, wherein the contact time of the compositions and the endoscope is between 1 and 15 minutes.

3. The method of claim 1, wherein the temperature of the compositions is between 5 and 55° C.

4. The method of claim 1, wherein the step of contacting the endoscope with the compositions comprises spraying, rinsing, or immersion.

5. The method of claim 1, wherein the antimicrobial composition comprises 0.001 to 0.5% by weight of peroctanoic acid, based on the total antimicrobial composition.

6. The method of claim 1, wherein the antimicrobial composition further comprises 0.0001 to 2.5% by weight of hydrogen peroxide, based on the total antimicrobial composition.

7. The method of claim 1, wherein the antimicrobial composition further comprises a complexing component for polyvalent metal ions.

8. The method of claim 1, wherein the method takes place in an automatic treatment process.

9. The method of claim 1, wherein the fatty acid comprises octanoic acid.

10. The method of claim 1, wherein the antimicrobial composition further comprises a hydrotrope.

* * * * *